US00PP18429P2

(12) United States Plant Patent
Oudolf

(10) Patent No.: US PP18,429 P2
(45) Date of Patent: Jan. 15, 2008

(54) ***ECHINACEA* PLANT NAMED 'FATAL ATTRACTION'**

(50) Latin Name: *Echinacea purpurea*
Varietal Denomination: Fatal Attraction

(75) Inventor: Petrus Hendricus Oudolf, Hummelo (NL)

(73) Assignee: Future Plants Licentie B.V., Lissenbroek (NL)

( * ) Notice: Subject to any disclaimer, the term of this patent is extended or adjusted under 35 U.S.C. 154(b) by 0 days.

(21) Appl. No.: 11/499,812

(22) Filed: Aug. 5, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Echinacea* plant named 'Fatal Attraction', characterized by its compact and upright plant habit; moderately vigorous growth habit; freely flowering habit; large single inflorescences with red purple-colored ray florets; and strong dark purple-colored peduncles that hold the inflorescences above the foliar plane.

2 Drawing Sheets

Botanical designation: *Echinacea purpurea.*
Cultivar denomination: 'Fatal Attraction'.

BACKGROUND OF THE INVENTION

The present invention relates to a new and distinct cultivar of *Echinacea* plant, botanically known as *Echinacea purpurea,* and hereinafter referred to by the name 'Fatal Attraction'.

The new *Echinacea* originated from an open-pollination of an unnamed selection of *Echinacea purpurea,* not patented, as the female, or seed, parent with an unknown selection of *Echinacea purpurea,* as the male, or pollen, parent. The new *Echinacea* was discovered and selected by the Inventor as a single flowering plant from within the progeny of the stated open-pollination grown in a controlled environment in Hummelo, The Netherlands in 2001.

Asexual reproduction of the new *Echinacea* by divisions in a controlled environment in Hummelo, The Netherlands since 2002, has shown that the unique features of this new *Echinacea* are stable and reproduced true to type in successive generations.

SUMMARY OF THE INVENTION

The cultivar 'Fatal Attraction' has not been observed under all possible environmental conditions. The phenotype may vary somewhat with variations in environment such as temperature and light intensity, without, however, any variance in genotype.

The following traits have been repeatedly observed and are determined to be the unique characteristics of 'Fatal Attraction'. These characteristics in combination distinguish 'Fatal Attraction' as a new and distinct cultivar of *Echinacea:*

1. Compact and upright plant habit.
2. Moderately vigorous growth habit.
3. Freely flowering habit.
4. Large single inflorescences with red purple-colored ray florets.

5. Strong dark purple-colored peduncles that hold the inflorescences above the foliar plane.

Compared to plants of the female parent selection, plants of the new *Echinacea* are more compact and are more freely flowering.

Plants of the new *Echinacea* can be compared to plants of the *Echinacea* cultivar Rubinstern, not patented. In side-by-side comparisons conducted in Lisserbroek, The Netherlands, plants of the new *Echinacea* differed from plants of the cultivar Rubinstern in the following characteristics:

1. Plants of the new *Echinacea* were more compact and more uniform than plants of the cultivar Rubinstern.
2. Peduncles of plants of the new *Echinacea* were dark purple in color whereas peduncles of plants of the cultivar Rubinstern were green in color.
3. Ray florets of plants of the new *Echinacea* were darker red purple in color than ray florets of plants of the cultivar Rubinstern.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of a typical flowering plant of 'Fatal Attraction' grown in an outdoor nursery.

The photograph on the second sheet is a close-up view of typical inflorescences of 'Fatal Attraction'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Lisserbroek, The Netherlands during the summer in an outdoor nursery and under conditions and practices which approximate those generally used in commercial *Echinacea* production. During the production of the plants, day temperatures ranged from 14° C. to 32° C. and night temperatures ranged from 7° C. to 14° C. Measurements and numerical values represent averages for typical flowering plants. Plants were about one year old when the photographs and description were taken.

Botanical classification: *Echinacea purpurea* cultivar 'Fatal Attraction'.

Parentage:

*Female parent.*—Unnamed selection of *Echinacea purpurea,* not patented.

*Male parent.*—Unknown selection of *Echinacea purpurea,* not patented.

Propagation:

*Type.*—By divisions.

*Time to produce a rooted young plant.*—About two months at 18° C. to 20° C.

*Root description.*—Fine, fibrous; light brown to white in color.

*Rooting habit.*—Freely branching.

Plant description:

*Plant form/growth habit.*—Compact, upright and uniform plant habit; inverted triangle; freely basal branching with inflorescences held above the foliage on strong peduncles. Moderately vigorous growth habit.

*Plant height.*—About 57 cm.

*Plant diameter or spread.*—About 47 cm.

*Lateral branches.*—Length: About 54.6 cm. Diameter: About 5 mm. Internode length: About 4.8 cm. Aspect: Mostly upright. Strength: Strong. Texture: Pubescent; rough. Color: 187A.

Foliage description:

*Arrangement.*—Alternate, simple.

*Length, basal leaves.*—About 16 cm.

*Length, stem leaves.*—About 9.1 cm.

*Width, basal leaves.*—About 7.7 cm.

*Width, stem leaves.*—About 2.8 cm.

*Shape, basal leaves.*—Ovate; apex, acute; base, attenuate.

*Shape, stem leaves.*—lanceolate; apex, acute; base, attenuate.

*Margin.*—Irregularly serrate.

*Texture, upper and lower surfaces.*—Pubescent; rough.

*Venation pattern.*—Pinnate.

*Color.*—Developing foliage, upper surface: 137B. Developing foliage, lower surface: 137C. Fully expanded foliage, upper surface: 137A; venation, 145A. Fully expanded foliage, lower surface: 137C; venation, 145B.

*Petiole length, basal leaves.*—About 15.2 cm.

*Petiole length, stem leaves.*—About 1.7 cm.

*Petiole diameter, basal leaves.*—About 3 mm.

*Petiole diameter, stem leaves.*—About 2 mm.

*Petiole color, upper and lower surfaces.*—144A; towards the base, 187A.

Inflorescence description:

*Appearance.*—Rotate single inflorescence form with ray and disc florets. Inflorescences positioned above the foliage on strong peduncles. Inflorescences face upright. Freely flowering habit; about three inflorescences develop per lateral branch. Inflorescences not persistent.

*Fragrance.*—Very faint; sweet.

*Time to flower.*—Plants flower continuously from late July to late September in The Netherlands.

*Post-production longevity.*—Inflorescences maintain good substance for about five weeks on the plant and for about two weeks as a cut flower.

*Inflorescence bud.*—Height: About 5 mm. Diameter: About 1 mm. Shape: Narrowly oblong. Color: N186C.

*Inflorescence size.*—Diameter: About 8.9 cm. Depth (height): About 3.3 cm.

*Ray florets.*—Shape: Oblanceolate. Length: About 3.8 cm. Width: About 8 mm. Apex: Emarginate. Base: Attenuate. Texture, upper and lower surfaces: Smooth, glabrous. Number of ray florets per inflorescence: About 36 arranged in one or two whorls. Color: When opening, upper surface: 71A; towards the base, slightly darker. When opening, lower surface: 61A; towards the apex, slightly darker. Fully opened, upper surface: 71B; towards the base, slightly darker. Fully opened, lower surface: 61B to 61C; towards the base, slightly darker.

*Disc florets.*—Shape: Tubular; apex dentate. Length: About 8 mm. Diameter: About 2 mm. Number of disc florets per inflorescence: About 400. Color: Immature: 197A tinted with 152A to 152B. Mature: 197A tinted with 152A to 152B.

*Receptacle spines.*—Quantity: One per disc floret. Length: About 1.2 cm. Width: About 1 mm. Shape: Linear. Apex: Sharply acute. Color: Towards the base, 144A to 144B; towards the apex, 53A.

*Phyllaries.*—Quantity per inflorescence: About 40 in about four whorls. Length: About 8 mm. Width: About 2 mm. Shape: Lanceolate. Apex: Acute; strongly reflexed. Margin: Entire. Texture, upper and lower surfaces: Densely pubescent. Color, upper and lower surfaces: 137B.

*Peduncles.*—Length: About 19.4 cm. Diameter: About 4 mm. Strength: Strong. Aspect: Mostly upright. Texture: Pubescent; rough. Color: 187A.

*Reproductive organs.*—Androecium: Quantity per disc floret: Three. Anther shape: Linear. Anther length: About 1 mm. Anther color: 151C. Pollen amount: Abundant. Pollen color: 14A. Gynoecium: Pistil length: About 5 mm. Stigma shape: Cleft; reflexed. Stigma color: 144A. Style length: About 4 mm. Style color: 144A. Ovary color: 145C. Fruits: Length: About 8 mm. Diameter: About 1 mm. Color: 161B. Seeds: Length: About 2 mm. Diameter: About 1 mm. Color: N199B.

Disease/pest resistance: Plants of the new *Echinacea* have not been shown to be resistant to pathogens and pests common to *Echinacea.*

Garden performance: Plants of the new Clematis have exhibited good tolerance to rain and wind and have been observed to be suitable for USDA Zones 4 to 9.

It is claimed:

1. A new and distinct *Echinacea* plant named 'Fatal Attraction' as illustrated and described.

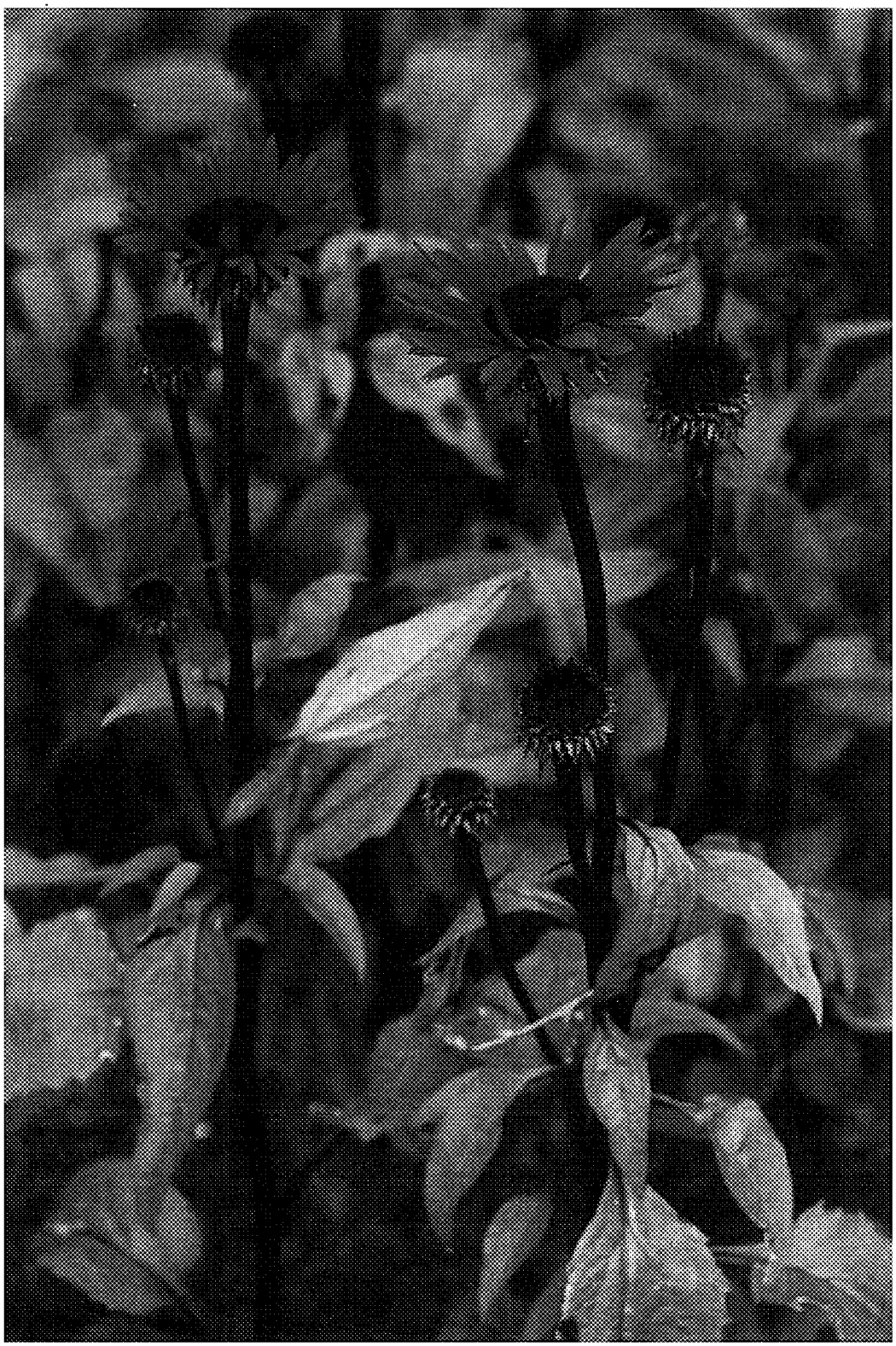

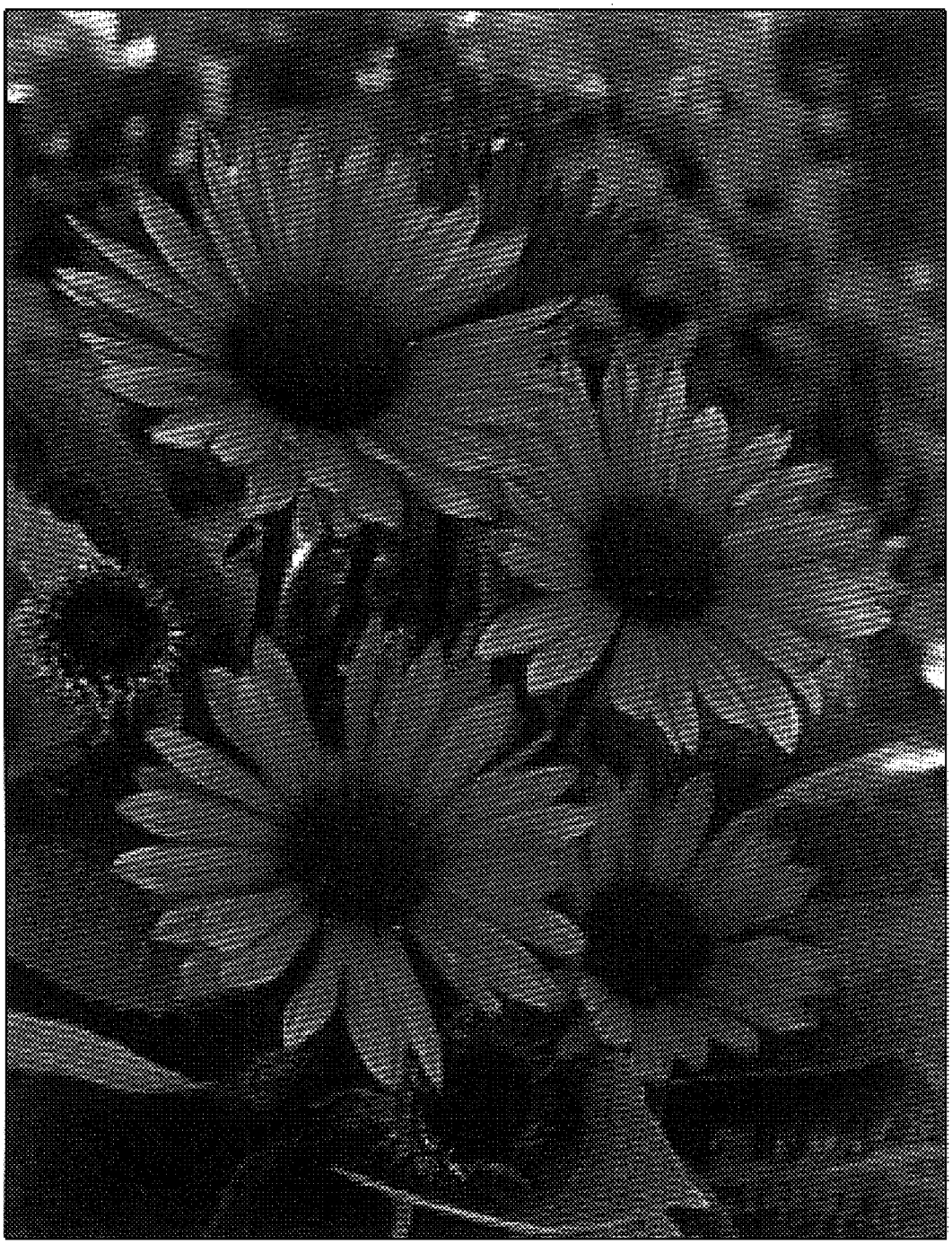

* * * * *